(12) United States Patent
Katz et al.

(10) Patent No.: US 8,750,973 B2
(45) Date of Patent: Jun. 10, 2014

(54) METHOD AND SYSTEM FOR DETECTING P-WAVES IN THE SURFACE ECG SIGNAL

(75) Inventors: Amos Katz, Lehavim (IL); Nahum Noam Weissman, Petach Tikva (IL); Yaniv Zigel, Omer (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 685 days.

(21) Appl. No.: 12/954,964

(22) Filed: Nov. 29, 2010

(65) Prior Publication Data

US 2011/0137190 A1 Jun. 9, 2011

Related U.S. Application Data

(60) Provisional application No. 61/272,986, filed on Nov. 30, 2009.

(51) Int. Cl.
*A61B 5/04* (2006.01)

(52) U.S. Cl.
CPC .................................. *A61B 5/04* (2013.01)
USPC ........................................................ 600/509

(58) Field of Classification Search
CPC ........... A61B 5/0002; A61B 5/02; A61B 5/04
See application file for complete search history.

(56) References Cited

U.S. PATENT DOCUMENTS

2009/0076402 A1* 3/2009 Hoium et al. ................. 600/515

\* cited by examiner

*Primary Examiner* — Eric D. Bertram
*Assistant Examiner* — Elizabeth K So
(74) *Attorney, Agent, or Firm* — Roach Brown McCarthy & Gruber, P.C.; Kevin D. McCarthy

(57) ABSTRACT

The invention provides an ECG system and apparatus for detecting P-waves even in the patients with arrhythmia. The system is capable of obtaining sufficient data from eight leads and to display an ECG construct with marked or emphasized P-waves.

14 Claims, 18 Drawing Sheets

| | Sinus | | | All rhythms | |
|---|---|---|---|---|---|
| Correlation threshold | Sensitivity | Precision | Correlation threshold | Sensitivity | Precision |
| 0.92 | 91.7% | 100% | 0.93 | 75.8% | 98.9% |
| 0.88 | 97.6% | 94.3% | 0.89 | 85.1% | 97.7% |
| 0.8 | 100% | 75.2% | 0.84 | 89.8% | 94.1% |

Preprocessing:

Phase One:

Phase Two:

Phase Three:

METHOD AND SYSTEM FOR DETECTING P-WAVES IN THE SURFACE ECG SIGNAL

REFERENCE TO CO-PENDING APPLICATIONS

Priority is claimed as a non-provisional of U.S. provisional patent application Ser. No. 61/272,986, filed on Nov. 30, 2009.

FIELD OF THE INVENTION

The present invention relates to a method and system for detecting P-waves in the ECG signals, particularly in the ECG of patients suffering from cardiac arrhythmias, enabling better diagnosis of heart diseases.

BACKGROUND OF THE INVENTION

The electrical heart activity is usually characterized by employing a multitude of electrode pairs, each pair providing a potential difference called a lead. Each lead is considered to represent the electrical activity of the heart from a different spatial angle. A 12-lead ECG is frequently used. The potential changes are plotted against time in the electrocardiogram. The heart activity as seen in an electrocardiogram (ECG) signal is regularly composed of three main components: P-wave, QRS wave complex, and T-wave, wherein the first component is associated with the atrial activity (AA) and the last two components with the ventricular activity (VA) (see FIG. 1). Analysis of the ECG and locating P-waves in the ECG signal are a crucial task in identifying arrhythmias and in diagnosing them, including, for example, differentiating between supra-ventricular arrhythmia and ventricular arrhythmia. Various methods have been proposed for detecting ECG components, but the detection of the P-waves is still an unsolved problem. P waves may be hidden in QRS complexes or T waves, and the AA is relatively difficult to detect since the VA has much more energy. It is known that misdiagnosis rate in arrhythmias may go as high as 30% [Shiovich A. et al.: Am. J. Med. Sci. 340 (2010) 271-5]. The cardiologist is often forced to insert electrodes into the patient's body to obtain the missing information.

Various approaches of atrial extraction from ECG signals include techniques of average beat subtraction (when improved methods comprise spatiotemporal QRST cancellation), localized search area (searching for P wave outside the QRS-T complexes), blind source separation (Independent Component Analysis—ICA). Principal Component Analysis (PCA), and semi-invasive approaches. The different approaches have different shortcomings; the average beat subtraction relies on the assumption of fixed shape QRS complexes, the ICA and PCA methods rely on the independency of the sources (non-correlatedness in PCA), and the localized search relies on the assumption that the QRS or T wave do not hide the P wave. It is therefore an object of the invention to locate P-waves along the ECG without invasive techniques, only from the surface measurements.

It is another object of the invention to provide an ECG signal with marked or emphasized P-waves, thereby assisting the professional in arriving to a correct diagnosis, particularly in regard to subjects suffering with arrhythmia.

It is a still further object of the invention to simplify the ECG measurement process.

Other objects and advantages of present invention will appear as description proceeds.

SUMMARY OF THE INVENTION

This invention provides a system for noninvasive measuring ECG signals produced by the heart of a human subject, and for detecting P-wave in said signals, comprising i) measuring means consisting of at least 9 electrodes, enabling to detect a potential difference at a plurality of points on the skin of said subject during a predetermined time interval (lead signal or lead), providing at least 8 lead signals; ii) electronic circuitry for amplifying said lead signals, reducing noise, converting the lead signals to data and transferring the data to storage means; iii) storage means consisting of an electronic memory for storing all data obtained in measuring said lead signals, for storing software used in processing said signals, and for storing all data resulting from said processing; iv) processing means (processor) for calculating linear combinations of said at least eight lead signals, while maximizing energy ratio between a predetermined marked time segment and other segments, and while providing an ECG construct with emphasized P-wave; and v) presenting means for graphical presenting said lead signals and said ECG constructs in a printed form or on display.

Said measuring means comprise, in a preferred embodiment of the invention, a software for performing the steps of i) storing said at least 8 lead signals as at least eight signal height-time functions in said predetermined time interval; ii) calculating a linear combination of said at least eight functions; iii) segmenting said linear combination into time segments, one of which is a predetermined time segment, and calculating a cost function of the energy ratio between said predetermined segment and all other segments; and iv) repeating steps ii) and iii) in order to maximize said cost function.

In one embodiment of the invention, 9 or 10 electrodes may be employed, and 12 surface ECG signals are obtained; the desired P-waves can be detected using from 8 to 12 of said signals. The SUMER technique enables to detecting the P-Waves by employing merely 8 of said 12 signals.

Said measuring means may consist of merely 9 electrodes providing 8 lead signals, compared to the standard number of 10 electrodes providing 12 signals. In a preferred system according to the invention, said measuring means comprise 8 leads and said processor comprises SUMER software technique. The system of the invention is advantageously employed for measuring ECG signals in patients suffering from arrhythmia. Said processor preferably includes a software for calculating linear combinations of eight leads, which combination converges to a signal that has the maximum energy ratio between a predetermined marked time segment and all other segments in the ECG signals. In one aspect of the invention, said predetermined segment is marked manually by an experienced person. In other important aspect of the invention, said predetermined segment is marked automatically by said processing means, employing, for example, techniques comprising unsupervised clustering. Said processor preferably separates atrial activity from ventricular activity, and emphasizes the atrial activity in said construct signal and in said lead signals. The invention relates to a system for measuring ECG signals, comprising i) measuring means providing 8 lead signals; ii) electronic circuitry amplifying said signals and converting them to data to be stored; iii) storage means storing said data, the data after processing, and reference (comparison) data characterizing ECG signals of patients suffering from arrhythmias; iv) processor comprising technique SUMER transforming said lead signals to ECG construct signal with emphasized P-waves in the whole of said time interval; and v) presenting means marking the positions of P-waves in at least one of said lead signals in the whole of said time interval, and optionally suggesting arrhythmia types with similar profiles; vi) thereby assisting in diagnosing an arrhythmia in said subject and substantially lowering the misdiagnosis rate for patients with heart arrhythmias.

The invention provides an ECG apparatus for detecting P-wave in ECG signals, comprising i) measuring means consisting of 9 electrodes, providing 8 lead signals during a predetermined time interval; ii) electronic circuitry for amplifying said lead signals, reducing noise, converting the lead signals to data and transferring the data to storage means; iii) storage means for storing measured signals, software for processing said signals, and data resulting from said processing; and iv) processing means using technique SUMER for calculating linear combinations of said eight leads, while maximizing energy ratio between a predetermined marked time segment and other segments in said time interval, and v) displaying means showing an ECG construct with emphasized P-waves, and at least one of said lead signal with P-waves marked in the whole of said time interval.

The invention provides a noninvasive diagnostic method for detecting an arrhythmia in a subject, and for differentiating between various arrhythmia types, comprising i) measuring 8 ECG lead signals; ii) amplifying said lead signals, reducing noise, converting the lead signals to data and transferring the data to storage means; iii) storing all data obtained in measuring said lead signals, software comprising technique SUMER for processing said signals, all data resulting from processing the data, and comparison data of ECG signals for subjects with arrhythmias; iv) processing the signals, comprising presenting said 8 lead signals as eight signal-time functions in said predetermined time interval, determining within said time interval a time segment to serve as a predetermined marked segment in the SUMER technique, generating linear combinations of said eight signal-time functions and calculating a cost function of the energy ratio between said predetermined segment and all other segments within said time interval, while aiming at maximizing said cost function and selecting a linear combination as an ECG construct with emphasized P-waves; and v) displaying said construct and at least one of said lead signals with P-waves marked along the whole of said time interval; and optionally comparing the obtained data with comparison ECG signals of subjects suffering with known types of arrhythmia. Said predetermined segment is marked manually by an experienced person; alternatively, it is marked automatically, using the method of unsupervised clustering, being performed by said a suitable software, possibly said SUMER. Said arrhythmia may be, for example, atrial fibrillation, atrial flutter, AVNRT, and AVRT.

BRIEF DESCRIPTION OF THE DRAWINGS

The above and other characteristics and advantages of the invention will be more readily apparent through the following examples, and with reference to the appended drawings, wherein:

FIG. 2. shows locating the P-wave on an ECG by a system and method according to the invention.

FIG. 3. shows an embodiment of locating P-wave on the ECG according to the invention.

FIG. 4. demonstrates some features of the processing process according to the invention, namely it is shown how the linear combination is forced to converge to a synthetic signal.

FIG. 10. presents processing of signals shown in FIG. 9, wherein

FIG. 11. shows an example of processing an ECG signal comprising atrial fibrillation.

FIG. 14. demonstrates how the SUMER technique emphasizes a signal of interest (for example P-wave); FIG. 14A is an ECG signal with denoted segments A and B supposed to represent a P-wave, and segments C and D supposed to respectively represent R and T waves; FIGS. 14B to 14E show results of signal processing performed in accordance with the invention, employing technique SUMER, when as a peak of interest is denoted sequentially peak A, B, C, and D (four different marking windows, predetermined marked segments, denoted in FIG. 14A)

FIG. 16. relates to the sensitivity and precision of the technique SUMER when using different correlation threshold (center method)

FIG. 17. shows effects of various thresholds on the number of proposed relevant signals.

DETAILED DESCRIPTION OF THE INVENTION

It has now been found that surprisingly good results can be obtained in detecting P-wave even from the ECG signals of patients suffering from arrhythmias. A new system and method, comprising measuring an eight-lead ECG signal, and processing the signal by a technique called SUMER, enables to substantially lower the misdiagnosis rate for patients with heart arrhythmias. A new apparatus is provided in accordance with the new findings.

The invention provides a system for detecting P-wave in the ECG signal of a subject, regardless the patient's anamnesis, comprising measuring means and processing means, the measuring means may include a electrocardiograph for collecting data from eight leads, and a processing means including a software for separating atrial activity from ventricular activity in said ECG signal. Said software constructs a linear combination of said at least eight leads, which combination converges to a signal that has the maximum energy ratio between a predetermined marked segment in the ECG and other non-marked segments. The resulting construct-ECG signal emphasizes the P-waves along the whole employed time interval, thereby assisting the physician to arrive at the correct diagnosis. Said predetermined segment may be, in one aspect of the invention, marked manually by an experienced person; in another aspect of the invention, the predetermined segment may be found and marked automatically by said processing means.

It was found by the inventors, that when SUMER processes said linear combinations and looks for a maximum in said energy ratio, it finds a global maximum, without any possibility to be "misled" to any local maxima. This finding enables efficient application of SUMER in emphasizing the P-waves. The term "energy ratio" is used herein for a signal ratio, being the ratio of two signals in two different time segments (subintervals); the marked segment should have a lot of atrial activity or energy in the enhanced AA signal (=high atrial signal), whereas the non-marked segment should have low energy of said AA signal (=low atrial signal).

Figure 1:
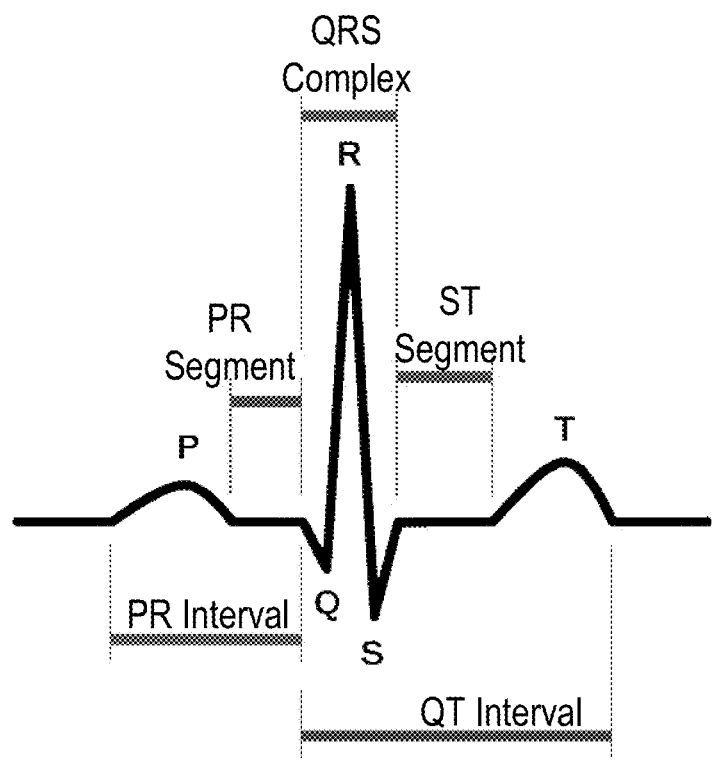
FIG. 1. shows the cardiac cycle and its components.
Figure 2A:
FIG. 2A shows an ECG signal with the P-wave indicated with arrows; the vertical lines delimit a P-wave, manually marked.
Figure 2B:
FIG. 2B shows a signal after processing according one embodiment of the invention, employing SUMER technique, emphasizing the P-waves.
Figure 3A:
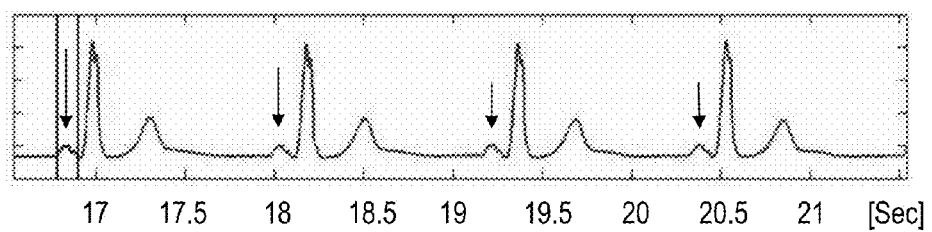
FIG. 3A shows a sinus rhythm with P-waves indicated by arrows, the vertical lines delimiting a P-wave.
Figure 18:
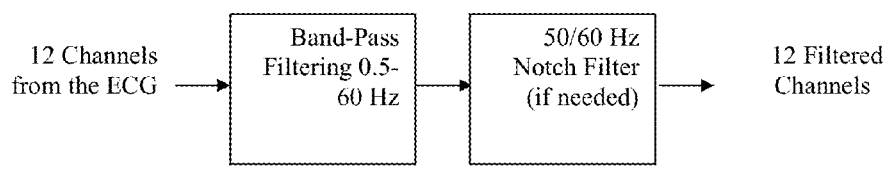
FIG. 18. is a flowchart showing a method of detecting P-wave, as described on page 9.
Figure 18:
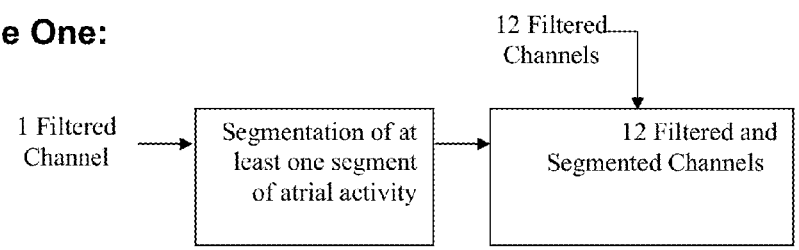
Figure 18:
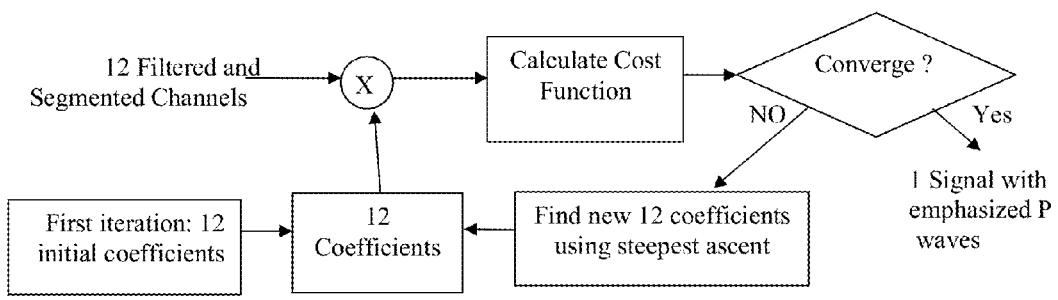
Figure 18:
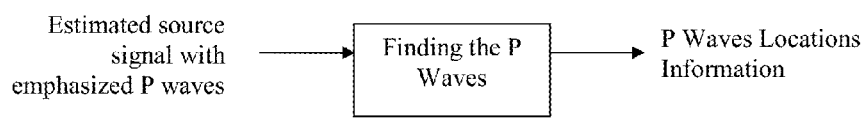

In one embodiment of the invention, the method of detecting P-wave includes several phases (FIG. 18). In preprocessing phase 0, ECG signals are filtered. In phase 1, manual segmentation of the ECG signals is effected to atrial activity area and non-atrial activity area. In phase 2, a calculation is effected, using the algorithm looking for the best linear combination which will give the maximum ratio between the energy of the area that has been marked as atrial activity area and the energy of the non-atrial activity area, thereby obtaining a signal with emphasized P waves and reduced QRS and T waves. In phase 3, a physician evaluates the construct and the original ECG record, locating and checking the P waves in the original electrocardiogram. In said phase 1, at least one P wave is manually marked in the ECG signal record. The physician may segment the signal into AA segments (P-waves) and NAA (non-AA) segments (FIG. 3a). The technique called SUMER, which is a part of this invention, may be then applied, including the algorithm aiming at finding λ coefficients, where λ is the number of leads used in collecting the ECG. In a method according to the invention, λ is at least 8. For the sake of the following example, λ is 12. Thus, said algorithm aims at finding at least 8 weights coefficients, namely 12 coefficients for 12 ECG lead signals in the following example, the linear combination using these weights would produce an output signal that should emphasize AA:

$$\text{out}(l) = \sum_{i=1}^{12} a_i \text{lead}_i(l) \quad (1)$$

Where out is the output signal, $a_i$ is the weight coefficient of lead i, is the i-th lead signal and l is the sample index. The algorithm subtracts the mean of every segment. For instance, if there is one AA segment and two NAA segments, the algorithm subtracts the mean from the at least 8 signals in the AA segment and from the 16 signals in the NAA segments. In said phase 2, said algorithm chooses 12 coefficients randomly (initial values). The cost function is now computed, which is the energy ratio between the marked and the non-marked segments in the output signal.

$$f(a_1, a_2 \ldots a_{12}) = \frac{\sum_{n=1}^{N}\left(\sum_{i=1}^{12} a_i G_i(n)\right)^2}{\sum_{m=1}^{M}\left(\sum_{i=1}^{12} a_i R_i(m)\right)^2} \quad (2)$$

Where $G_i$ is all the marked segments of lead i after concatenating them into one signal with N samples. $R_i$ is all the non-marked segments of lead i after concatenating them into one signal with M samples. Next, the algorithm finds the coefficients that produce the maximum cost function. Gradient ascent method is performed to find the optimal coefficients by adding iteratively the gradient of the function to the coefficients until convergence is obtained:

$$(a_1, a_2, \ldots, a_{12})_{p+1} + \mu \nabla f = (a_1, a_2, \ldots, a_{12})_p \quad (3)$$

Where $\nabla f$ is the gradient of the cost function, μ is the step size and p is the iteration index. The gradient is defined by:

$$\nabla = \left(\frac{\partial}{\partial a_1}, \frac{\partial}{\partial a_2}, \ldots, \frac{\partial}{\partial a_{12}}\right) \quad (4)$$

And every partial derivative is defined by:

$$\frac{\partial f}{\partial a_i} = \frac{\partial}{\partial a_i} \frac{\sum_{n=1}^{N}\left(\sum_{j=1}^{12} a_j G_j(n)\right)^2}{\sum_{m=1}^{M}\left(\sum_{j=1}^{12} a_j R_j(m)\right)^2} = \quad (5)$$

-continued $$\frac{\left(\sum_{n=1}^{N}\sum_{j=1}^{12}2a_jG_i(n)G_j(n)\right)\left(\sum_{m=1}^{M}\left(\sum_{j=1}^{12}a_jR_j(m)\right)^2\right)}{\left(\sum_{m=1}^{M}\left(\sum_{j=1}^{12}a_jR_j(m)\right)^2\right)^2} -$$

$$\frac{\left(\sum_{m=1}^{M}\sum_{j=1}^{12}2a_jR_i(m)R_j(m)\right)\left(\sum_{n=1}^{N}\left(\sum_{j=1}^{12}a_jG_j(n)\right)^2\right)}{\left(\sum_{m=1}^{M}\left(\sum_{j=1}^{12}a_jR_j(m)\right)^2\right)^2}$$

Figure 3B:
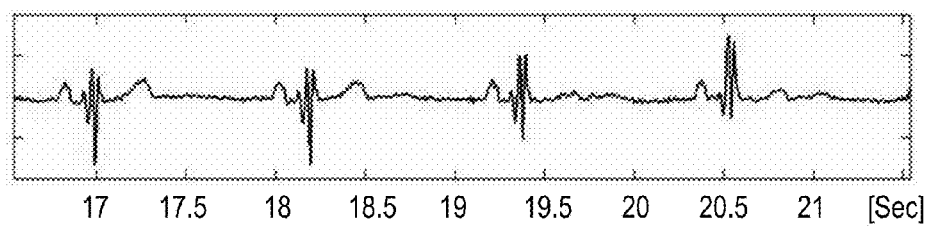
FIG. 3B shows a result produced by the method of the invention, emphasizing P-waves.
Figure 3C:
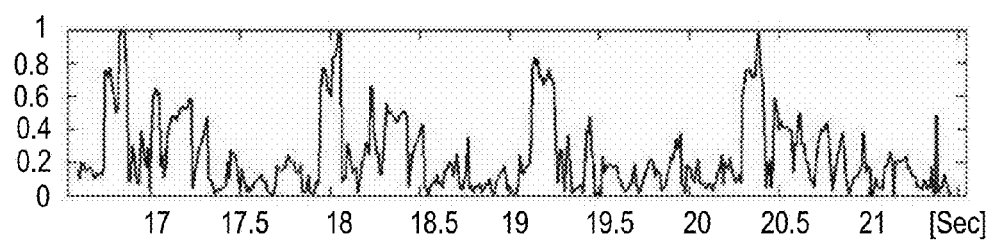
FIG. 3C shows further magnifying of the P-wave in another possible processing route, method of the moving window, which decides that a segment contains a P-wave if the value of the result signal in the segment is bigger than a certain threshold, and the correlation signal is bigger than a certain threshold.
Figure 17A:
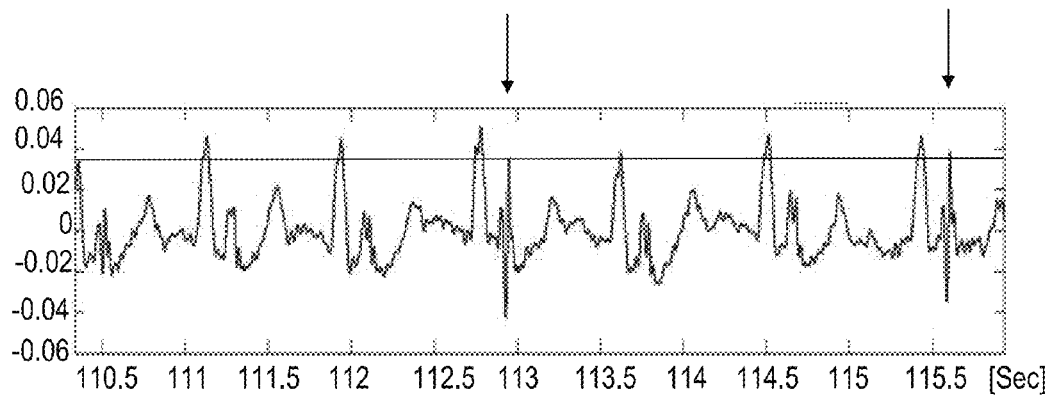
FIG. 17A shows applying SUMER algorithm on a sinus rhythm at a threshold of 0.03, the arrows indicate two false positives.
Figure 17B:
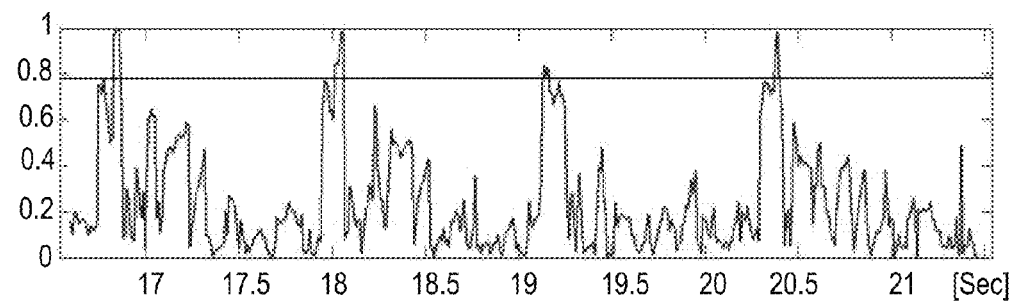
FIG. 17B relates to a threshold of 0.8, all P-waves appear without any false positives.

After the optimization, coefficients are obtained that should produce a signal with emphasized AA (FIG. 3B). The presence of P-wave in the original ECG signal may be further represented also in a correlation-signal as follows. A moving window is applied on the original ECG signal, and its similarity with the obtained construct-signal is evaluated, using Pearson's linear correlation coefficient (FIG. 3C). Thus, there are two indications for the presence of P-wave in a certain segment: the construct signal with the emphasized p-waves and the correlation-signal. If the value of the result signal in a specified segment is bigger than a certain threshold, and the correlation signal is bigger than a certain threshold, the decision may be that the segment contains a P-wave. In the signal with the emphasized P-waves, the segment may be considered to comprise a P-wave if its signal values are higher than a certain percentage of the whole signal. Using threshold on the emphasized P-waves signal may find the p-waves as can be seen in FIG. 17A, choosing a threshold of 0.03 identify all the P waves but have 2 false alarms which are indicated with arrows. In the correlation signal, a value of 0.8 as an appropriate threshold identifies all the P-waves without false positives (FIG. 17B).

The method of the invention may comprise 12 lead electrograph, but a 8-lead device according to the invention will provide needed results. In one embodiment of the invention, the segmentation in the above phase 1 can be performed automatically. The thresholds can be chosen according to the needs of the skilled practitioner. The thresholds can be an adaptively selected threshold instead of a fixed one. In other embodiments of the invention, the segmentation may comprise marking the P-wave as AA and the T wave as NAA, while wiping the QRS complex out from the cost function calculation. The result will emphasize the P wave in respect of the T waves but not in the respect of the QRS complex.

The invention relates to an ECG apparatus comprising 9 noninvasive electrodes, enabling 8 leads. Traditionally, 9 to 12 leads were employed, but the invention establishes that 8 leads may provide the same information if employed together with the data processor according to the invention, which uses the technique of Separation Using Maximum Energy Ratio (SUMER). The device comprises electrodes, electronics amplifying the signals obtained by electrodes, data storage medium for storing the signal intensity-time information, and calculation unit. The calculation unit comprises a software for processing the information including the software for performing SUMER. The SUMER technique provides a cost function (energy ratio), and calculates linear combinations of the lead signals till obtaining a maximum for said cost function. Said energy ratio compares the signal value along the time-signal ECG curve with the signal value in certain predetermined segment defined as a segment containing a P-wave, said predetermined segment being marked either manually or automatically. Said manual marking is performed by a skilled practitioner, said automatic marking by said calculation unit using, for example, unsupervised clustering technique. Similarly, as in the P-wave detection, the clustering technique compares outputs in various segments to each other, and then the locations are classified into different groups by their similarity to each other, providing groups of locations such as containing QRS-complexes, P-waves, and T-waves.

In one aspect of the invention, a predetermined time segment of an ECG signal, used in the calculations performed by SUMER technique, is marked by an expert manually. In other aspect of the invention, said predetermined segment is marked automatically, using SUMER broadened with additional software elements. Such elements may be, for example, found among known methods [for example, Duda R. et al.: Pattern Classification (2 edition ed.). Wiley-Interscience (2001)]. In pattern classification, the aim is to classify some elements to different groups. In the first step, feature extraction, some characteristics of the element are obtained, which are relevant to the classification (for instance, dominant frequency of segment in a signal is a characteristic that can differentiate between P-wave and QRS). Next, using the characteristic of the element, the classifier decides to which group the element belongs. The classifier is designed using prior knowledge about the groups. The process of using data (training data) to determine the classifier is referred to as training the classifier. There are many different procedures for training classifiers, for instance, using the training data for estimating the distribution of every group we can design a classifier which examines an element and find from which distribution the element's characteristics have most likely come. Another classifier is the nearest neighbor classifier which looks for the element in the training data which is the closest to the examined element in the sense of similar characteristics and then the examined element is classified to its nearest neighbor's group. Cluster analysis is a method of unsupervised learning. The clustering is the assignment of a set of elements into clusters. The term 'unsupervised' refers to the fact that we don't have a-priori knowledge about the characteristics of the different clusters; the classification is managed automatically using the distances between the elements' characteristics. The distance can be the Euclidean/Manhattan/Mahalanobis, or other distance between the elements calculated using their characteristics values. The method of the invention may use, for example, agglomerative hierarchical clustering which has the following steps: i) every element is defined as a cluster; ii) created is a distance matrix (the distance between two clusters can be the minimum/maximum/mean or other distance between elements of each cluster) in which Aij element is the distance between clusters i and j; iii) the two closest clusters are found and merged into one cluster; iv) if the stop criterion is fulfilled then the procedure stops, otherwise step ii is started again. The stop criterion can be the situation when all the clusters have a distance from each other bigger than a certain value, or when the number of clusters reaches certain value.

The invention relates to a method for detecting P-waves in the ECG record of subjects suffering from heart conditions, comprising measuring ECG signals by at least 8 leads, and processing the signals by employing SUMER technique. The method of the invention was applied in various practical and model situations by the present inventors. In various examples, ECG records of subjects exhibiting various arrhythmias (sinus, atrial flutter, atrial fibrillation, AVRT, AVNRT) were processed. ECG records were processed to provide 32 segments of 10 seconds each. The results showed good enhancement, for example, in case of sinus rhythm, atrial flutter, and AVRT; in the P-wave detection of those rhythms, sensitivity of 89.8% and precision of 94.1% was obtained. In the case sinus rhythm alone, sensitivity of 97.6% and precision of 94.3% were obtained. Unsupervised clustering was applied on sinus rhythm signals and showed good results in clustering the QRS, T, and P waves into different groups.

The invention relates to improved device and method for detecting P-wave in the ECG of a subject, one of the improvement resulting from employing a processing unit which provides a construct signal with emphasized P-waves. For providing the construct signal many linear combinations are calculated to optimize the energy cost, and these calculations surprisingly showed that more than 8 leads does not substantially improve the extracted information. That finding led to developing the improved system and method of the invention including ECG comprising 8-leads. A new ECG apparatus is provided, comprising 9 electrodes and 8 lead signals. Working in an 8 dimensional space instead of 10 or 12, as in previous systems, is more computational demanding, and devices having 10 or more electrodes are more complex than the preferred device of the invention having 9 electrodes.

The system of the invention is capable of detecting P-wave even in complex ECG signals of arrhythmia patients. The system advantageously works with 8-leads, but it can provide important results with any practical number of electrodes. The system can emphasize the P-waves significantly, in many diagnostic situations, and the method and apparatus of the invention provide superior results when comparing with existing methods and apparatuses. In some cases the QRS complex and T-waves are almost not visible (for example, QRS and T-waves in atrial fibrillation and T-waves in atrial flutter), in other cases they are visible but their amplitude is suitably reduced in comparison to the P-waves.

Since SUMER uses different approach than other separation and detection methods, combining SUMER with existing techniques will produce important results, and such a combination is a part of the invention. The invention will be further described and illustrated by the following examples.

EXAMPLES

Experimental Setup

Signals from the GE Cardiolab IT were used; it produces standard 12 lead ECG. Further, invasive measurements were used from the high right atrium (HRA), taken in Barzilai medical center with ethical approval for the study form Barzilai medical center ethics committee. Locations of P-waves (for marking the P-wave and for P-wave detection evaluation) were defined using the HRA measurements. Also signals from the St Petersburg INCART 12-lead Arrhythmia Database (physionet.org database) have been used.

Sampling frequency of the signals were 977 and 257 Hz for the Cardiolab and St Petersburg signals, respectively. The following 10-sec segments were used: nine segments of sinus rhythm from four patients; six segments of atrial fibrillation from two patients; six segments of AVNRT (atrioventricular nodal reentry tachycardia) from three patients; five segments of atrial flutter from two patients; three segments of AVRT (atrioventricular reentry tachycardia) from one patient; and two cases of premature atrial contraction from one patient.

In the pre-processing phase, the ECG signals were filtered using a band-pass with band of 0.5-60 Hz. Elimination of the 50 Hz power supply noise was carried out. All the algorithms were developed using the Mathworks Matlab software.

Example 1

Figure 4A:
FIG. 4A is an ECG signal.
Figure 4B:
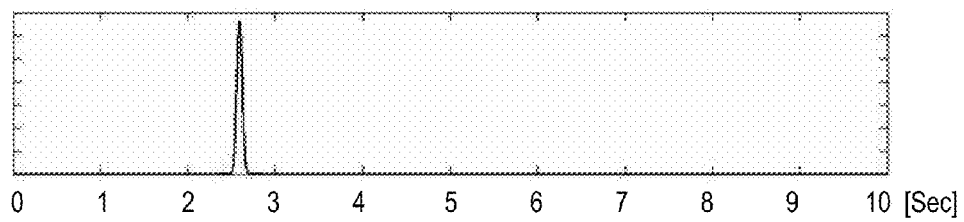
FIG. 4B is a synthetic signal.
Figure 4C:
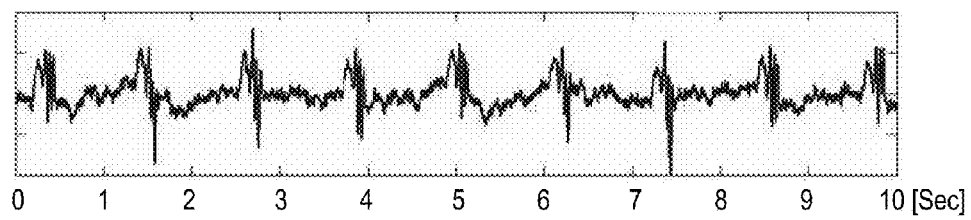
FIG. 4C is an output of the separation, carried out according one embodiment of the invention.

The use of the SUMER algorithm was demonstrated in this example on an 8-lead signal (FIG. 4A), by using a synthetic AA signal (FIG. 4B). Assuming that there is a linear combination of the 8 lead signals that reconstructs the AA signal, the way was looked for to force a linear combination to converge to a signal that is similar to the AA signal. At first, using a-priori knowledge of the P-wave locations (using the HRA signal in some cases, or simply by looking at lead signal in cases like sinus rhythm) was used to mark the location of the P-waves. Next, chosen was a certain shape of for a rectangular or Gaussian peak with width of the P-waves in the signal. The shape should imitate a P-wave. Reconstructed signal emphasized the P-waves (FIG. 4C).

Example 2

Figure 5A:
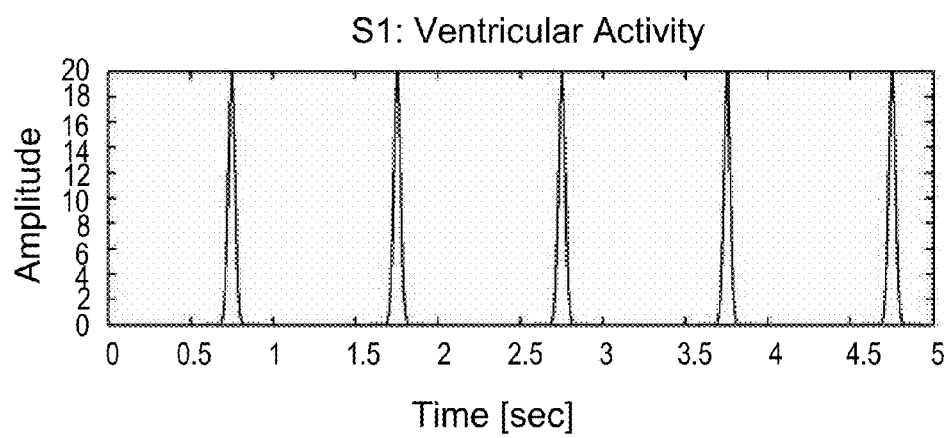
FIG. 5. presents simulation of A) ventricular activity and B) atrial activity.
Figure 5B:
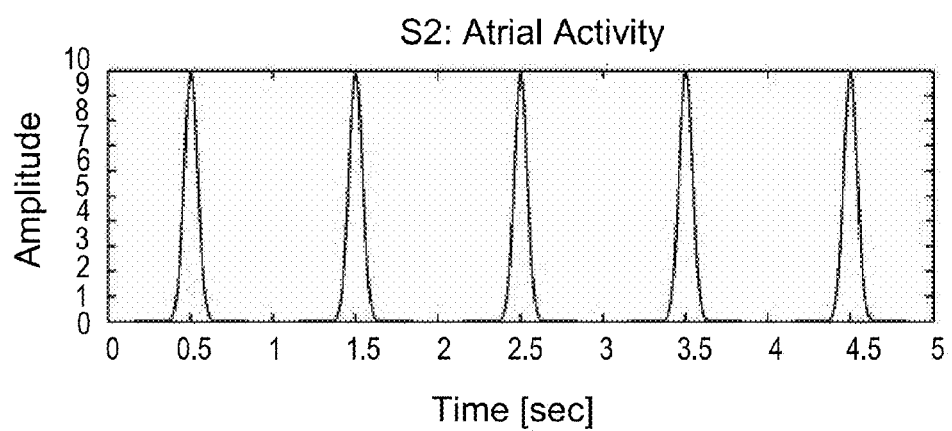
Figure 6A:
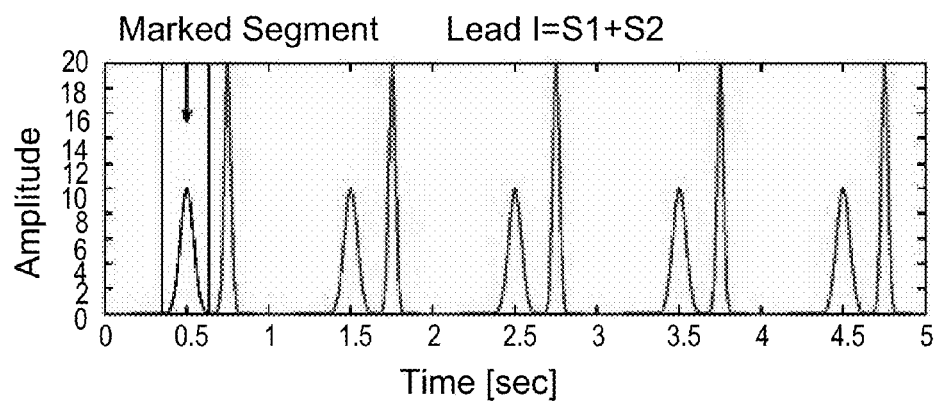
FIG. 6. presents two different linear combinations of the source signals, such as shown in FIG. 5; a segment containing the P-wave is marked for the SUMER technique.
Figure 6B:
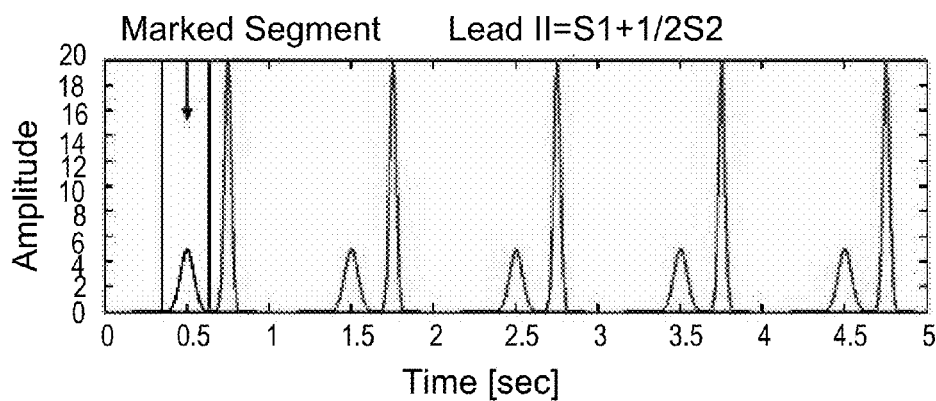
Figure 7:
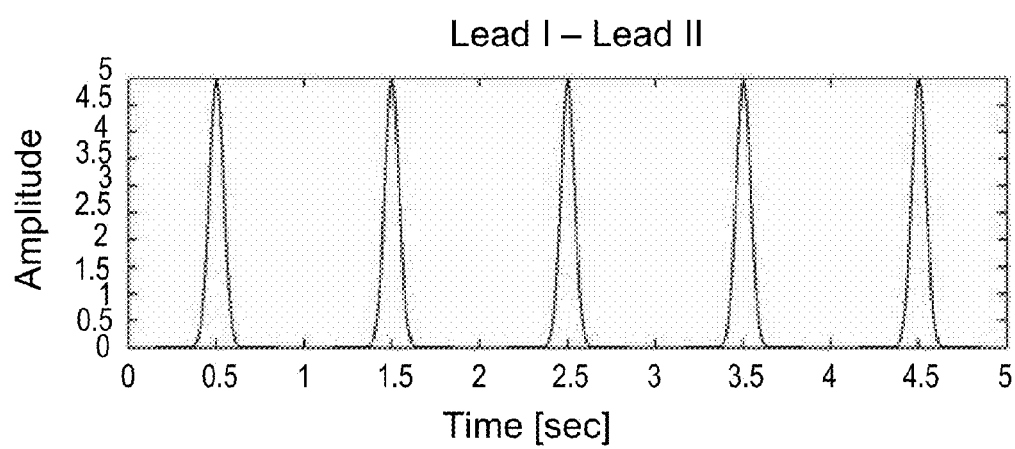
FIG. 7. shows the result produced by SUMER technique from the simulations such as shown in FIG. 6, producing an idealized signal of atrial activity.

This example demonstrates some features of employing linear combinations of ECG signals, and simulates the work of SUMER technique. It is supposed that signal S1 is associated with ventricular activity and signal S2 with atrial activity (FIG. 5). Surface ECG measures the heart activity using two leads, denoted I and II, measuring the heart activity from different sites (angles). For the sake of this example, it is supposed that lead I is equal to S1+S2 and lead II is equal to S1+0.5*S2. In other words, lead I is a linear combination of the sources with weight coefficients (1,1) and lead II is a linear combination of the sources with weight coefficients (1,0.5) (FIG. 6). Now, one segment in the simulated ECG lead is marked as P-wave, and a linear combination of the two leads is searched for that will produce the highest ratio between the marked segment's energy and the non-marked segment's energy. The energy ratio will get its maximum when the QRS complexes will reduce to zero. The amplitude of the P-waves doesn't have an influence on the energy ratio since the energy of the marked P-wave and the energy of the non-marked P-waves have a constant ratio of 1/4 (one P-wave against 4). The desired signal can be obtained from a linear combination of the two leads with derivable coefficients. The obtained signal contains the atrial activity source signal only (FIG. 7).

Example 3

Figure 8:
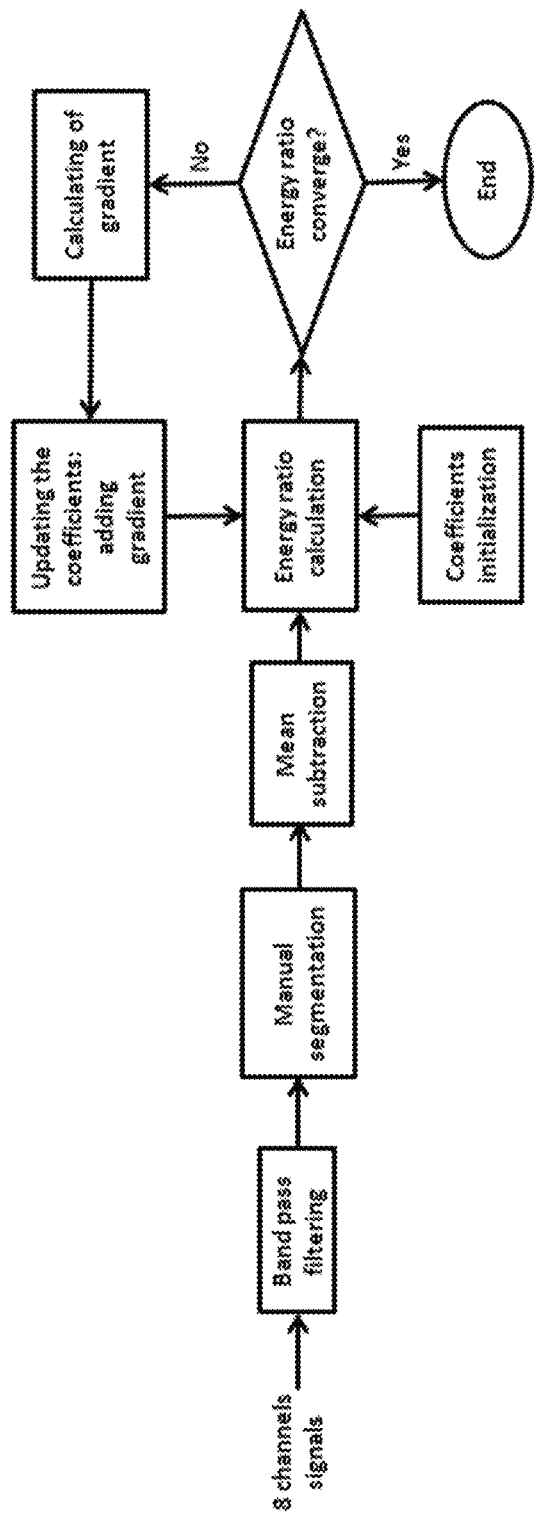
FIG. 8. is a flowchart of processing a source signal, provided by a 8-leads ECG measurement, in accordance with one embodiment of the invention, employing SUMER technique.
Figure 9A:
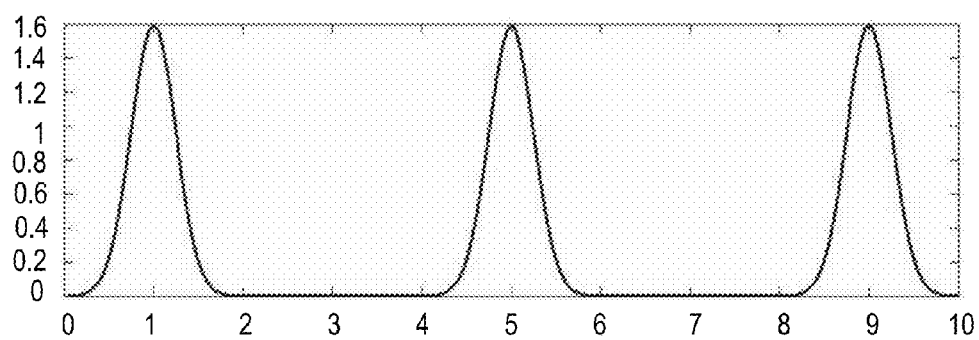
FIG. 9. presents a simulated signal of A) ventricular activity and B) atrial activity to be processed according to various considered ways.
Figure 9B:
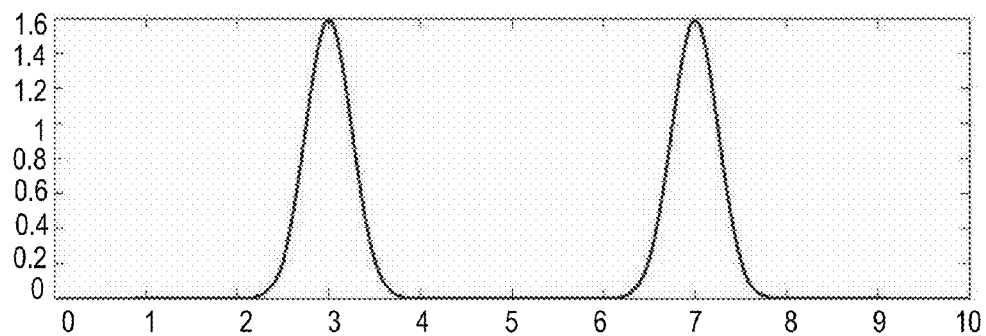
Figure 10A:
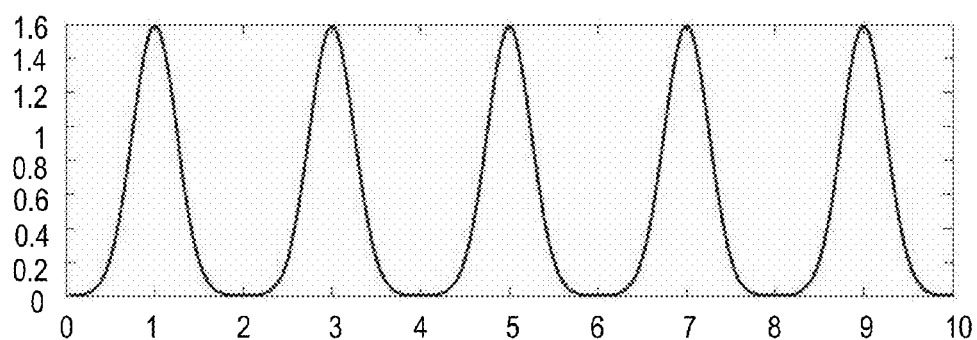
FIG. 10A shows simulated lead 1 being AA+VA.
Figure 10B:
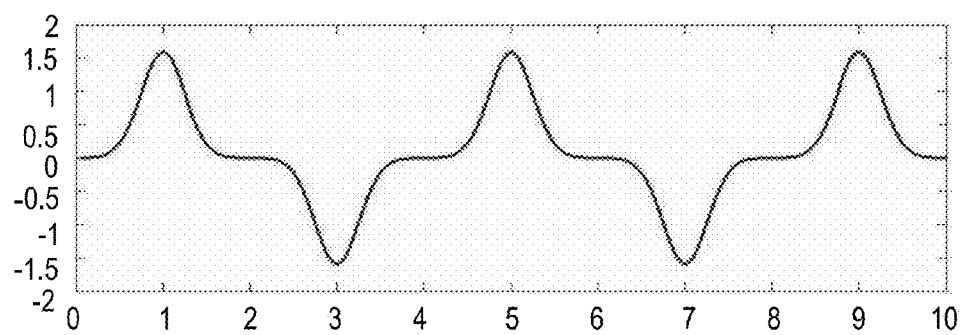
FIG. 10B shows simulated lead being VA-AA, the leads serving in calculating the cost function.

Applying SUMER (Separation Using Maximum Energy Ratio) technique on ECG signals is further demonstrated in this example. A flowchart is shown in FIG. 8. Employed are steps of filtering 8 channels, segmenting the channels into marked and non-marked segments (AA and NAA), subtracting of the mean of each segment, creating a cost function of the energy ratio between the AA segment and the NAA segment with initial coefficients for the linear combination, optimization of the cost function to its maximum by changing the coefficients using gradient ascent method until converging to a fixed value. In a simulation, there is atria-associated signal (FIG. 9A) and ventricles-associate signal (FIG. 9B); two lead signals are simulated as linear combination of the atrial and ventricular activity: Lead 1=AA+VA (FIG. 10A) and Lead 2=VA−AA (FIG. 10B). The solution to get only the AA is Lead1−Lead2. And the solution to get only the VA is Lead1+Lead2. So the coefficients ($c_1$, $c_2$) will give us the maximum ratio for the cost function if we mark part of the AA as marked in FIG. 10A. The maximum energy ratio in that case is 1 since we have one marked P-wave and one non-marked P-wave.

Figure 11A:
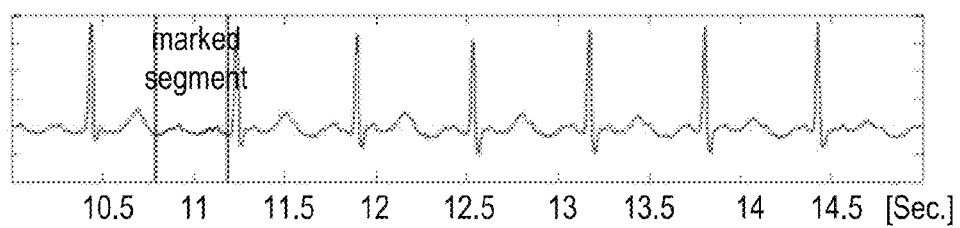
FIG. 11A is an ECG signal, the vertical lines denoting an expected segment of AA.
Figure 11B:
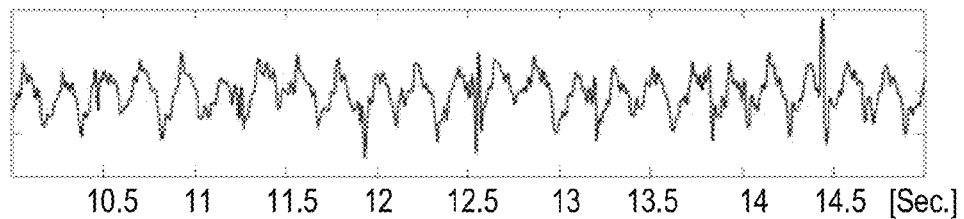
FIG. 11B shows an output of the SUMER technique.

In the same way, the technique is applied on a real ECG, for example ECG obtained for a patient with atrial fibrillation (FIG. 11A). The vertical lines denote the AA segment. The segments outside of the vertical lines are the NAA segments. The SUMER technique provides an output with emphasized signals assumed top be P-waves (FIG. 11B).

Example 4

Figure 12:
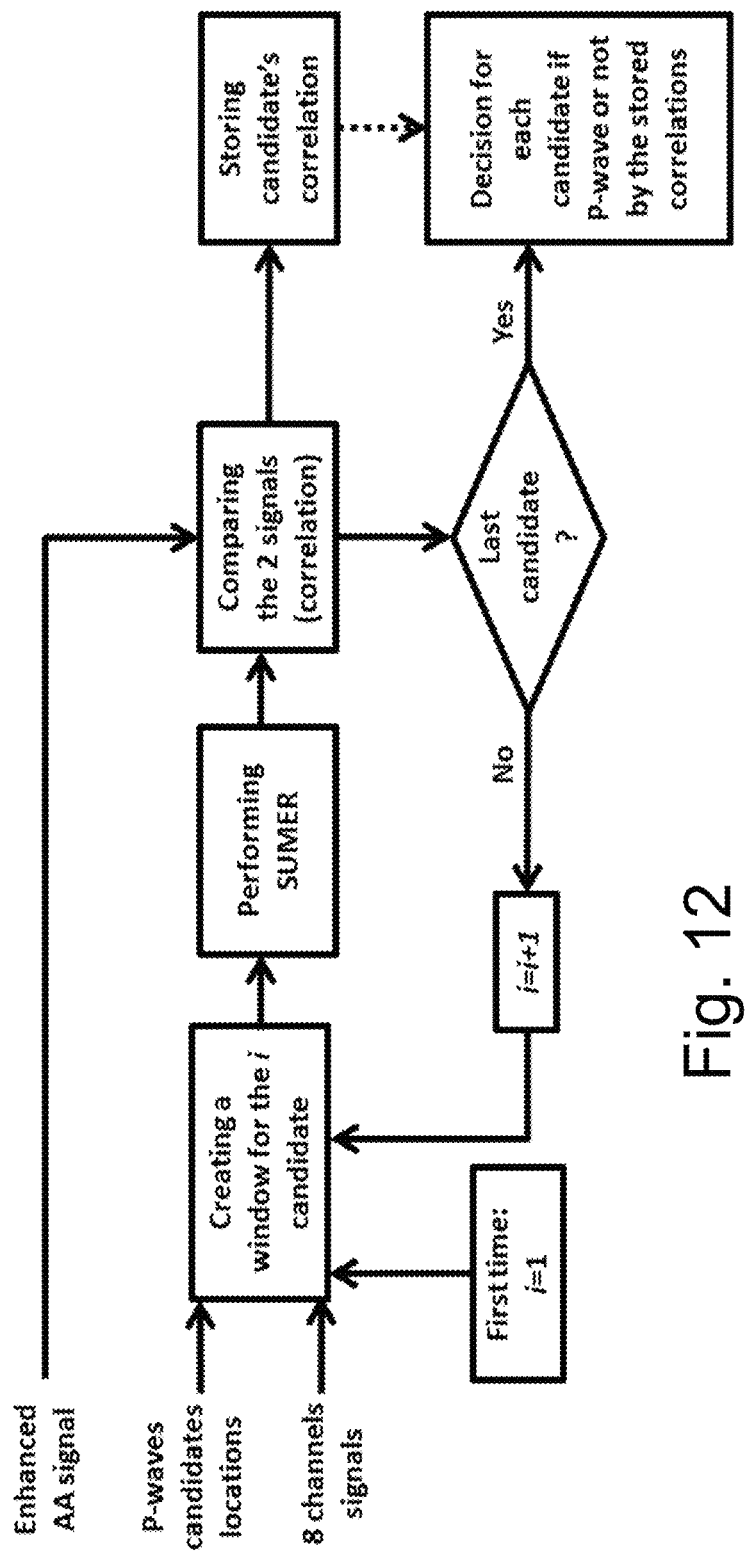
FIG. 12. is a flowchart for detecting P-wave in accordance with one embodiment of the invention; the input of P-waves candidates' locations is being used for checking a part of suspected locations and not every possible location in the ECG signal, the signal provided by a 8-leads ECG measurement.

Expanding SUMER to waves detection in the original ECG record is further elaborated. SUMER can be used for P-wave detection using the following steps (flowchart in FIG. 12): marking (manually) one P-wave in the ECG signal (by framing the wave in a segment of certain width) and performing SUMER while obtaining enhanced AA signal P(t); marking the beginning of the ECG signal with a window of the same width as the mentioned marked segment; performing SUMER and obtaining a candidate result signal denoted by C(t,i) when i is the candidate result signal index; moving the marking window a little step in time, updating i to i+1 and repeating the previous step until arriving to the end of the ECG signal; calculating the correlation coefficients for all the candidates signals C(t,i) with P(t) while obtaining a correlation coefficients signal; if a certain marking window contains a P-wave, C(t,i) for that window should contain emphasized P-waves and should have high correlation with P(t), and if not, C(t,i) has low correlation with P(t); by choosing a certain threshold the correlation coefficients signal should enable detecting the P-waves.

Example 5

Figure 13:
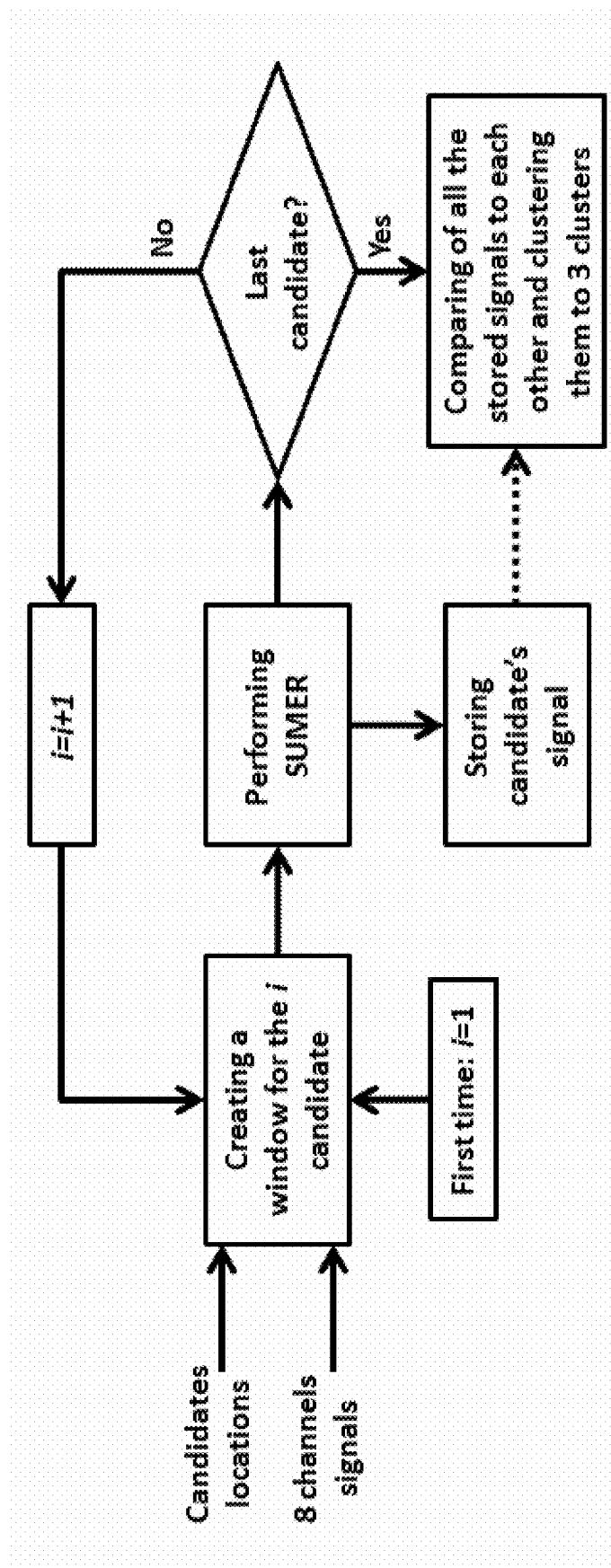
FIG. 13. is a flowchart for detecting P-wave in accordance with one embodiment of the invention, without manual denoting a P-wave, by means of unsupervised clustering of P-waves, T-waves and QRS complexes; the input of P-waves candidates' locations is being used if wishing to check only some suspected locations and not every possible location in the ECG signal.

Employing SUMER to waves detection in the original ECG record, without manual marking a predetermined segment supposed to comprise P-wave is elaborated (flowchart in FIG. 13). Unsupervised clustering using SUMER is employed. When relating to clustering of the ECG signal, what is meant is separating the signal into some clusters such as P-wave, QRS complexes, T-waves, etc. Different time segments in the signal (different locations in the ECG signal) are being grouped to different clusters. In supervised classification the results can be that we classify the P-wave locations, QRS locations and T-waves locations to three different classes with the labels "P", "QRS" and "T". In unsupervised clustering, the result is similar, obtaining several groups, but it is not known which group contains the P-waves, QRS waves, and T-waves. It must be determined what signals are in the clusters. Again, a moving window is used. For every step of the window, the window is segmented as AA and the rest of the signal as NAA. The location of the window is defined as its center. Now, an output signal is created using SUMER, and denoting P-wave if the window marks a P-wave or denote T-wave if it marks a T-wave, etc., while using Pearson's correlation coefficients between all the resulting signals, and getting an N×N distance matrix, where N is the number of windows having been used. Agglomerative hierarchical clustering is performed using the N×N distance matrix to cluster the different instances in the ECG signal to 3 different groups.

Example 6

Figure 14F:
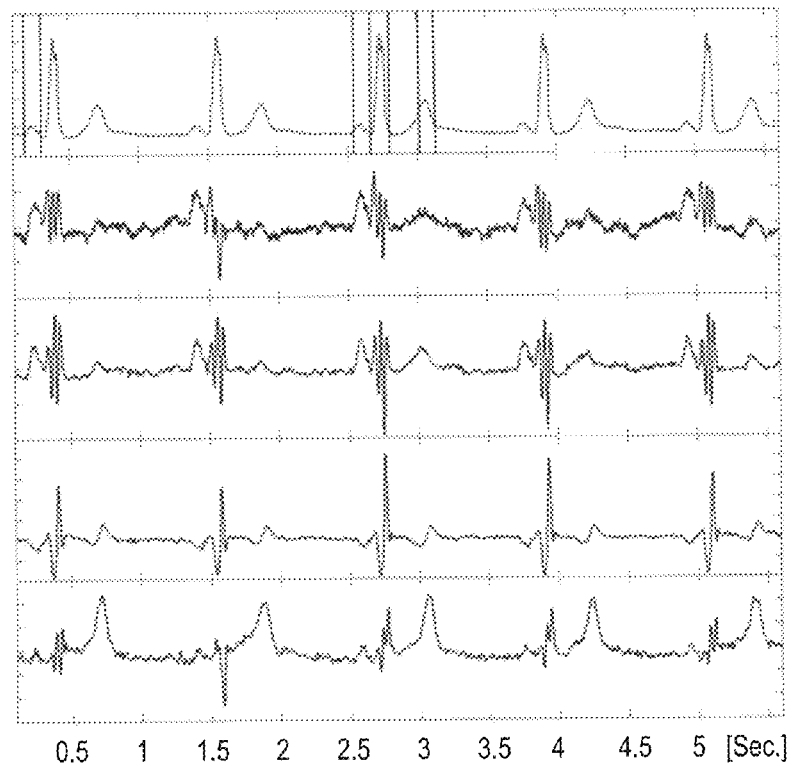
FIG. 14F is the correlation of the signal A to the outputs of every possible marking window, and as B signal is similar to A (the two emphasize P-waves)—their correlation is high while the correlations with C and D are low.
Figure 14F:
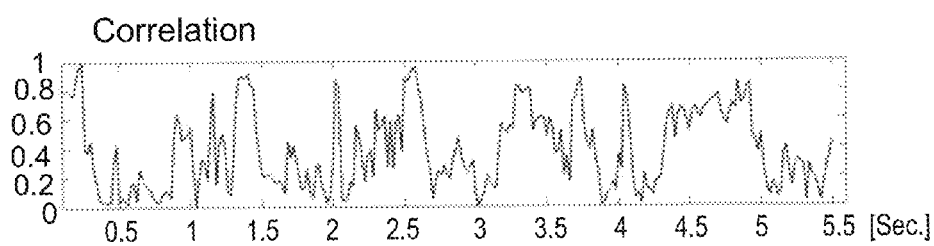

A general signal of any origin is processed (FIG. 14A). Any time, segment assumed to comprise an important wave and not other features is selected. Technique SUMER is employed for processing the signal, wherein said marked segment serves as the predetermined segment in the SUMER technique. Provided is a construct signal as already explained. Depending on which segment was predetermined, construct will emphasize relevant waves. This way P-wave may be located on the ECG record (FIGS. 14B and 14C), or waves of any other type (FIGS. 14D and 14 E). Additionally, a correlation construct may be obtained, for example for P-wave (FIG. 14F).

Example 7

Figure 15:
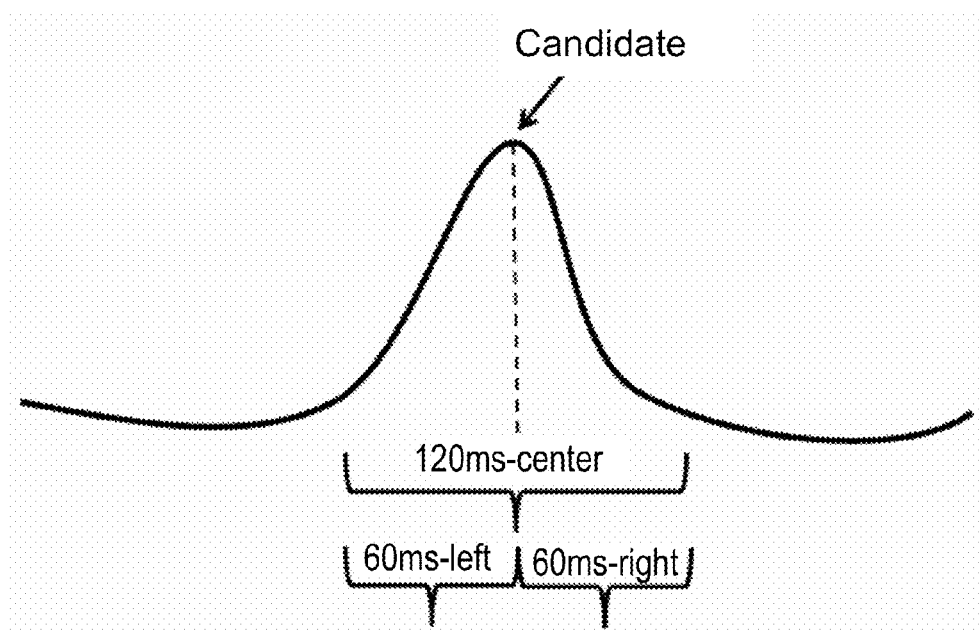
FIG. 15. magnifies a candidate peak (a location suspected as a P-wave) in the sinus according to technique SUMER, the candidate being submitted to a selection comprising the correlation threshold; shown are three marking windows being used to perform SUMER: center, right and left.

Evaluation a candidate for a P-wave is related to in this example. Three marking windows are considered (FIG. 15) for performing SUMER—center, right and left. For every candidate, the correlation of the output of the 120 ms marking window, as well as of the two 60 ms windows, is examined, and it is checked whether the correlation is higher than a certain threshold or not. Evaluation of the P-wave detection is based on Portet et al. [Portet F. Physiological Measurement 29 (2008) 141-55], but instead of 85 ms proximity as maximum for good detection, 60 ms is used. The evaluation is performed as follows. True positive (TP) is the number of P-waves detected in the proximity of 60 ms at most. False positive (FP) is the number of candidates that have been identified as a P-wave but do not in the proximity of 60 ms. False negative (FN) is the number of P-waves that have not been detected in the proximity of 60 ms. Then, calculated were sensitivity (Se), precision (Pr, also called positive predictivity), and error rate (ER), as follows:

$$Se = \frac{TP}{TP + FN} \quad (5.1)$$

$$Pr = \frac{TP}{TP + FP} \quad (5.2)$$

$$ER = \frac{FP + FN}{TP + FN + FP} \quad (5.3)$$

Figures 16A, 16B, 16C, 16D:
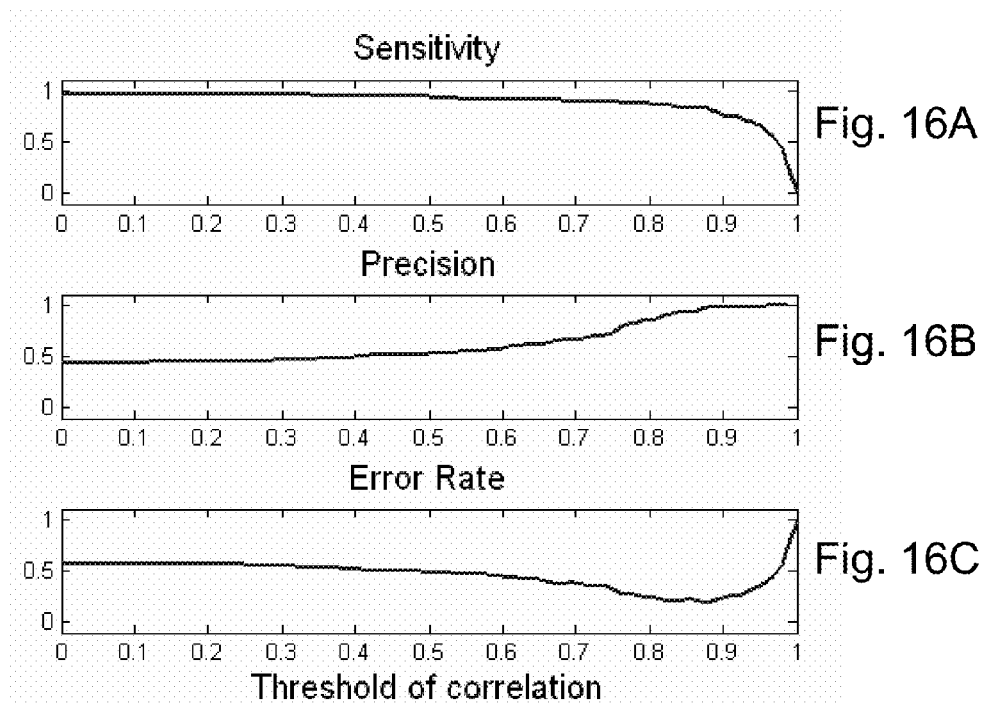
FIGS. 16A, 16B, and 16C respectively show sensitivity, precision, and error rate as functions of the threshold of correlation.
FIG. 16D is a table showing the dependence of sensitivity and precision on the correlation threshold for either sinus or all rhythms.

The values are shown in FIG. 16. Finding the best performance depends on the practical requirements, in regard to the number of false positive or false negative results. The table in FIG. 16B summarizes performances in the sinus case and in all other rhythms cases:

Example 7

It is shown in the example how applying various thresholds may affect the number of suggested relevant signals. When applying the SUMER algorithm on a sinus rhythm at a threshold of 0.03, all the P waves were identified, but also two false positives appeared (indicated with arrows in FIG. 17A). At a threshold of 0.8, all P-waves appear, without any false positives (FIG. 17B).

While the invention has been described using some specific examples, many modifications and variations are possible. It is therefore understood that the invention is not intended to be limited in any way, other than by the scope of the appended claims.

The invention claimed is:

1. A system for noninvasive measuring ECG signals produced by the heart of a human subject, and for detecting P-wave in said signals, comprising
   i) measuring means consisting of at least 9 electrodes, capable of detecting a potential difference at a plurality of points on the skin of said subject during a predetermined time interval (lead signal), providing at least 8 lead signals;

ii) electronic circuitry for amplifying said lead signals, reducing noise, converting the lead signals to data and for transferring the data to storage means;

iii) storage means consisting of an electronic memory for storing all data obtained in measuring said lead signals, for storing software used in processing said signals, and for storing all data resulting from said processing;

iv) processing means for calculating linear combinations of said at least eight lead signals and for segmenting said linear combination into time segments one of which is a predetermined marked time segment, followed by applying SUMER technique (Separation Using Maximum Energy Ratio) to calculate a cost function of the energy ratio between said predetermined segment and other segments within said time interval, to maximize said energy ratio and to provide an ECG construct with emphasized P-wave; and v) presenting means for graphical representation of said lead signals and said ECG constructs in a printed form or on display.

2. The system according to claim 1, wherein said measuring means consist of 9 electrodes, capable of providing 8 lead signals.

3. The system according to claim 1, wherein said measuring means comprise a software for performing the steps of
i) representing said at least 8 lead signals as eight signal-time functions in said predetermined time interval;
ii) calculating a linear combination of said at least eight signal-time functions;
iii) segmenting said linear combination into time segments, one of which is a predetermined time segment, and calculating a cost function of the energy ratio between said predetermined segment and all other segments; and
iv) repeating steps ii) and iii) in order to maximize said cost function.

4. The system according to claim 1, wherein said subject suffers from arrhythmia.

5. The system according to claim 1, wherein said processing means include a software for calculating linear combinations of eight leads, which combination converges to a signal that has the maximum energy ratio between a predetermined marked time segment and all other segments.

6. The system according to claim 1, wherein said predetermined segment is marked manually by an experienced person.

7. The system according to claim 1, wherein said predetermined segment is marked automatically by said processing means.

8. The system according to claim 1, wherein said measuring processing means separate atrial activity from ventricular activity, and emphasize the atrial activity in said construct signal and in said lead signals.

9. The system according to claim 1, comprising
i) measuring means providing 8 lead signals;
ii) electronic circuitry amplifying said signals and converting them to data to be stored;
iii) storage means storing said data, said data after their processing, reference (comparison) data characterizing ECG signals of patients suffering from arrhythmias, and a software for said calculating;
iv) processing means comprising technique SUMER, transforming said lead signals to ECG construct signal with emphasized P-waves in the whole of said time interval; and
v) presenting means marking the positions of P-waves in at least one of said lead signals in the whole of said time interval, and optionally suggesting arrhythmia types with similar profiles, as indicated by said reference data of patients suffering from arrhythmias;

thereby assisting in diagnosing an arrhythmia in said subject and substantially lowering the misdiagnosis rate for patients with heart arrhythmias.

10. An ECG apparatus for measuring ECG signals produced by the heart of a human subject, and for detecting P-wave in said ECG signals, comprising
i) measuring means consisting of 9 electrodes capable of detecting a potential difference at a plurality of points on the skin of said subject, providing 8 lead signals during a predetermined time interval;
ii) electronic circuitry for amplifying said lead signals, reducing noise, converting the lead signals to data and transferring the data to storage means;
iii) storage means for storing measured signals, software for processing said signals, and data resulting from said processing;
iv) processing means using technique SUMER for calculating linear combinations of said eight leads, while maximizing energy ratio between a predetermined marked time segment and other segments in said time interval and while providing an ECG construct with emphasized P-wave, and
v) displaying means showing an ECG construct with emphasized P-waves, and at least one of said leads with P-waves marked in the whole of said time interval.

11. A noninvasive diagnostic method for detecting an arrhythmia in a subject, and for differentiating between various arrhythmia types, comprising
i) measuring 8 ECG lead signals;
ii) amplifying said lead signals, reducing noise, converting the lead signals to data and transferring the data to storage means;
iii) storing all data obtained in measuring said lead signals, storing software comprising technique SUMER for processing said signals, storing all data resulting from processing the data, and storing comparison data of ECG signals for subjects with arrhythmias;
iv) processing the signals, comprising representing said 8 lead signals as eight signal-time functions in said predetermined time interval, determining within said time interval a time segment to serve as a predetermined marked segment in the SUMER technique, generating linear combinations of said eight signal-time functions and calculating a cost function of the energy ratio between said predetermined segment and all other segments within said time interval, while aiming at maximizing said cost function and selecting a linear combination as an ECG construct with emphasized P-waves; and
v) displaying said construct and at least one of said lead signals with P-waves marked along the whole of said time interval; and optionally comparing the obtained data with reference (comparison) ECG signals of subjects suffering with known types of arrhythmia.

12. The method according to claim 11, wherein said predetermined segment is marked manually by an experienced person.

13. The method according to claim 11, wherein said predetermined segment is marked automatically, using the method of unsupervised clustering, being performed by said SUMER.

14. The method according to claim 11, wherein said arrhythmia is atrial fibrillation.

* * * * *